United States Patent

Knaus et al.

Patent Number: 5,118,866
Date of Patent: Jun. 2, 1992

[54] PREPARATION OF POLYENE ALDEHYDES

[75] Inventors: Guenter H. Knaus, Ludwigshafen; Joachim Paust, Neuhofen, both of Fed. Rep. of Germany

[73] Assignee: BASF Aktiengesellschaft, Ludwigshafen, Fed. Rep. of Germany

[21] Appl. No.: 152,875

[22] Filed: Feb. 5, 1988

[30] Foreign Application Priority Data

Feb. 24, 1987 [DE] Fed. Rep. of Germany ....... 3705785

[51] Int. Cl.⁵ .................. C07C 45/00; C07D 319/06; C09F 5/00
[52] U.S. Cl. .................................. 568/447; 568/446; 549/375; 549/454; 554/120
[58] Field of Search ...................... 280/398; 260/405.5; 568/446, 447; 549/375, 454

[56] References Cited

U.S. PATENT DOCUMENTS 4,005,031  1/1977  Surmatis .
4,026,910  5/1977  Marbet .

FOREIGN PATENT DOCUMENTS 1068709  4/1960  Fed. Rep. of Germany .
337500   5/1959  Switzerland .

OTHER PUBLICATIONS

Synthesis 1976, pp. 65–75.
Houben-Weyl VII/1 (1954), p. 178.
Chem. Rev. 67, p. 188 (1967).
J. Chem. Soc. (1952), p. 1094.
Houben-Weyl V/1d, p. 13 (1972).
J. Am. Chem. Soc., vol. 106, pp. 3374–3376 (1984).
Lieb. Ann. der Chem. 1976, pp. 2194–2205.
Helv. Chim. Acta 49, p. 369, 1966.

Primary Examiner—Alan Siegel
Attorney, Agent, or Firm—Keil & Weinkauf

[57] ABSTRACT

Polyene aldehydes of the general formula I

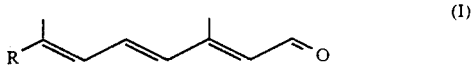

where R is

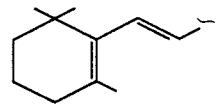

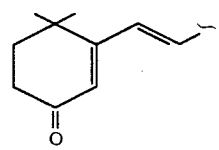

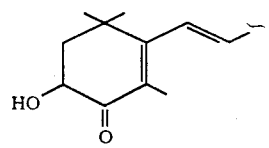

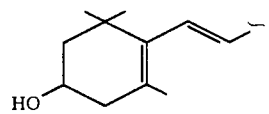

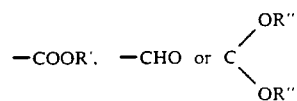

where R' is alkyl, aryl, aralkyl or cycloalkyl and, if desired, may be further substituted, and the radicals R" are each $C_1$–$C_4$-alkyl or together form —$CH_2$—$CH_2$— or —$CH_2$—$CH_2$—$CH_2$— bridges which, if desired, may be further substituted by $C_1$–$C_4$-alkyl, are prepared by catalytic oxidation of the corresponding polyene alcohol with oxygen or an oxygen-containing gas by a process wherein the oxidation is carried out in the presence of the catalyst system comprising 2,2,6,6-tetramethylpiperidine 1-oxide or 4-oxo-2,2,6,6-tetramethylpiperidine 1-oxide and copper(I) chloride.

7 Claims, No Drawings

PREPARATION OF POLYENE ALDEHYDES

The present invention relates to a process for the preparation of polyene aldehydes, in particular vitamin A aldehyde.

The conversion of a polyene alcohol into a polyene aldehyde is not a trivial reaction because the substrate to be converted is a very sensitive substance. As described in Synthesis 1976, page 65 et seq., in particular page 74, only a few of the compounds suitable for undergoing oxidation of α,β-unsaturated alcohols can therefore be used for the preparation of polyene aldehydes.

The ability of an oxidizing agent to oxidize sensitive polyene alcohols, for example vitamin A, vitamin A derivatives and carotenoids, to the aldehydes without isomerization, is often used for characterizing the particularly mild action of this reagent (cf. Synthesis 1976, page 65 et seq., in particular page 75, and Houben-Weyl VII/1 (1954), 178). Metal oxides, such as manganese dioxide or nickel peroxide, have proven particularly suitable reagents for the oxidation of polyene alcohols to the corresponding aldehydes.

Unfortunately, these oxidizing agents can only be used in heterogeneous form, so that their oxidation properties depend to a great extent on the distribution and the surface properties of the oxide used. Consequently, the yield may vary greatly from batch to batch (Chem. Rev. 67 (1967), 188). Furthermore, metal oxides having appropriate activity must be prepared by special processes (cf. DE-A-25 29 605 and DE-A-24 15 928). Another disadvantage of the metal oxides which must be stated is that they generally have to be used in large excess (cf. J. Chem. Soc. (1952), 1094), but at least in an equimolar amount, and furthermore the reaction times may be very long.

A process for the preparation of retinal, having the features stated in the preamble of claim 1, is described in CH-A-337 500. The oxidation is platinum-catalysed. The disadvantage of this process is that it is uneconomical. Relatively large amounts of platinum catalysts have to be used, and the yields obtained are nevertheless unsatisfactory. This is probably attributable, to a not insignificant extent, to the fact that the retinol skeleton contains a large number of oxidation-sensitive double bonds and allyl sites. It is for this reason that, very generally, it is advisable to work in the absence of oxygen when handling polyenes (cf. Houben-Weyl 5/1d, page 13 (1972)).

It is known that the catalyst system 2,2,6,6-tetramethylpiperidine 1-oxide and copper(I) chloride can be used for the oxidation of allylic alcohols (cf. J. Amer. Chem. Soc. 106 (1984), 3374-3376). However, when this catalyst system is used with sensitive polyene alcohols, the occurrence of isomerization and a substantial reduction in the yields of the desired product must be expected.

It is an object of the present invention to provide a process for the preparation of polyene aldehydes of the general formula I

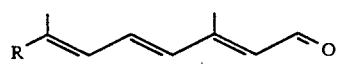

where R is

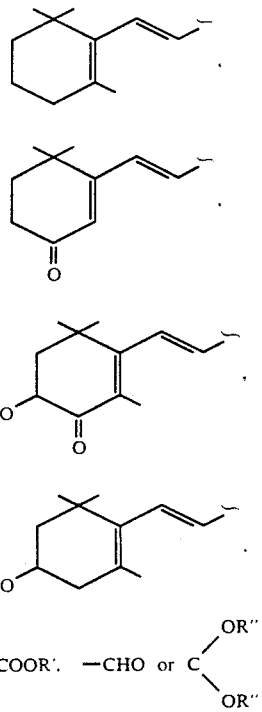

$$-COOR', \quad -CHO \text{ or } C\begin{array}{c}OR''\\OR''\end{array}$$

where R' is alkyl, aryl, aralkyl or cycloalkyl and, if desired, may be further substituted, and the radicals R" are each $C_1$-$C_4$-alkyl or together form $-CH_2-CH_2-$ or $-CH_2-CH_2-CH_2-$ bridges which, if desired, may be further substituted by $C_1$-$C_4$-alkyl, by catalytic oxidation of the corresponding polyene alcohol with oxygen or an oxygen-containing gas, by means of which process the sensitive polyene alcohols can be oxidized without significant isomerization and in excellent yields.

We have found that this object is achieved by a process of the stated type, wherein the oxidation is carried out in the presence of the catalyst system comprising 2,2,6,6-tetramethylpiperidine 1-oxide or 4-oxo-2,2,6,6-tetramethylpiperidine 1-oxide and copper(I) chloride.

In a preferred embodiment of the novel process, (all-E)-retinal is prepared from (all-E)-retinol.

In a particularly advantageous embodiment of the novel process, the reaction is carried out in the homogeneous phase in a solvent.

Particularly suitable solvents are organic solvents. N,N-dimethylformamide, N,N-dimethylacetamide, 1-methyl-2-pyrrolidone, N,N-dimethylpropyleneurea and N,N-dimethylethyleneurea are particularly preferred.

In a particularly advantageous embodiment of the novel process, the catalyst components 2,2,6,6-tetramethylpiperidine 1-oxide or 4-oxo-2,2,6,6-tetramethylpiperidine 1-oxide and copper(I) chloride are used in a molar ratio of from 1:0.5 to 1:3.

In another advantageous embodiment of the invention, the individual catalyst components are each used in an amount of from 1 to 10, in particular from 5 to 10, mol %, based on the polyene alcohol used.

The polyene aldehydes which can be prepared by the novel process are either compounds having useful biological activity, like vitamin A aldehyde, or key compounds for the preparation of important carotenoids. For example, retinal can be subjected to a Wittig reaction with triphenyl(retinyl)phosphonium salts to give beta-carotene which is a desirable compound (cf. DE-C-1 068 709). Furthermore, the β-apocarotenals are obtainable by subjecting retinal to Wittig reactions with (1,1-dimethoxy-3-methyl-2-butenyl)triphenylphosphonium chloride (cf. Lieb. Ann. Chem. 1976, 2194-2205). Ethyl 2,6-dimethyl-8-oxoocta-2,4,6-trien-1-oate can be reacted readily with triphenyl(retinyl)phosphonium chloride to give ethyl β-apo-8'-carotenate, which is a desirable food color (cf. Helv. Chim. Acta 49 (1966), 369).

Instead of the catalyst component 2,2,6,6-tetramethylpiperidine 1-oxide, it is also possible to use 4-oxo-2,2,6,6-tetramethylpiperidine 1-oxide, the same results being obtained. This is advantageous in that this compound is obtainable from ammonia and acetone in only two stages, making the process even more economical.

To carry out the reaction in practice, oxygen or an oxygen-containing gas is passed through a solution of the substance in one of the stated solvents, to which the catalyst system has been added. The reaction temperature is advantageously from 0° to 40° C., preferably from 20° to 40° C.

When the reaction is complete, the desired substance can be separated from the catalyst by chromatography, which, because of its low Rf value, is more advantageous in the case of the 4-oxo-2,2,6,6-tetramethylpiperidine 1-oxide used than in the case of 2,2,6,6-tetramethylpiperidine 1-oxide. In another version of the working up procedure, the desired substance is extracted by means of a suitable solvent from the reaction solution, which has been diluted with water or aqueous sodium chloride solution, and the residual amounts of catalyst are removed by shaking with a solution of sodium iodide in hydrochloric acid. The crude substance thus obtained can then be purified by crystallization or chromatography.

In the general formula I, R' may be alkyl, aryl, aralkyl or cycloalkyl. If desired, R' may be further substituted. Alkyl is, in particular, $C_1$-$C_{20}$-alkyl, particularly preferably $C_1$-$C_6$-alkyl. Aryl includes, in particular, phenyl and naphthyl. Aralkyl is, for example, $C_1$-$C_6$-alkylphenyl, in particular benzyl. Cycloalkyl may be, for example, $C_3$-$C_{12}$-cycloalkyl. Where R' is further substituted, the substituents may be $C_1$-$C_6$-alkoxy, OH, halogen or unsubstituted or substituted amino.

The radicals R" may be $C_1$-$C_4$-alkyl, in particular methyl, and may be identical or different. However, the radicals R" may furthermore be —$CH_2$—$CH_2$— or —$CH_2$—$CH_2$—$CH_2$— bridges and thus form a cyclic acetal. The bridges can, if desired, be monosubstituted or disubstituted by $C_1$-$C_4$-alkyl. An example is the radical

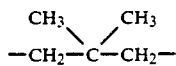

which gives the following acetal group.

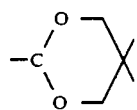

If the oxidizing agent used is an oxygen-containing gas, the latter is, in particular, air or is a gas mixture to which oxygen has been added or which has been enriched with oxygen.

The Examples which follow illustrate the invention.

EXAMPLE 1

Oxidation of retinol to retinal using 2,2,6,6-tetramethylpiperidine 1-oxide/copper(I) chloride as a catalyst From 50 to 60 ml of oxygen per minute were passed through a solution of 10.0 g (34.9 millimoles) of (all-E)-retinol and 545 mg (3.49 millimoles) of 2,2,6,6-tetramethylpiperidine 1-oxide in 75 ml of N,N-dimethylformamide, after the addition of 345 mg (3.49 millimoles) of copper(I) chloride, at room temperature. After 2 hours, the mixture was poured onto 150 ml of aqueous sodium chloride solution and extracted with methyl tert-butyl ether until the extraction solution was colorless. The extract was washed with water and dried with sodium sulfate, and the solvent was removed under reduced pressure. The residue was chromatographed rapidly over silica gel by means of methylene chloride to give 9.1 g (91.6% yield) of a product which contained less than 5% of the cis isomer and was shown to be pure by $^1$H-NMR. Crystallization from n-hexane gave 7.2 g (72.6% yield) of retinal having a melting point of 60°-62° C. and a UV value $E^1_1$ of 1,515 at 381 nm (ethanol).

EXAMPLE 2

Oxidation of retinol to retinal using 4-oxo-2,2,6,6-tetramethylpiperidine 1-oxide/copper(I) chloride From 50 to 60 ml of oxygen per minute were passed through a solution of 10.0 g (34.9 millimoles) of (all-E)-retinol and 594 mg (3.94 millimoles) of 4-oxo-2,2,6,6-tetramethylpiperidine 1-oxide in 75 ml of N,N-dimethylformamide, after the addition of 345 mg (3.49 millimoles) of copper(I) chloride, at room temperature. After 3 hours, the mixture was poured onto 150 ml of aqueous sodium chloride solution and extracted with methyl tert-butyl ether until the extraction solution was colorless. The extract was washed with water and dried with sodium sulfate, and the solvent was removed under reduced pressure. The residue was chromatographed rapidly over silica gel by means of 2:1 cyclohexane/ethyl acetate to give 8.8 g (88.7% yield) of a product which contained less than 5% of the cis isomer and was shown to be pure by $^1$H-NMR. Crystallization from n-hexane gave 6.9 g (69.5% yield) of retinal having a melting point of 60°-62° C. and a UV value $E^1_1$ of 1,520 at 381 nm (ethanol).

EXAMPLE 3

Oxidation of ethyl 8-hydroxy-2,6-dimethylocta-2,4,6-trien-1-oate with 2,2,6,6-tetramethylpiperidine 1-oxide/copper(I) chloride From 50 to 60 ml of oxygen per minute were passed through a solution of 30.0 g (142.7 millimoles) of ethyl 8-hydroxy-2,6-dimethylocta-2,4,6-trien-1-oate (isomer mixture) and 2.23 g (14.3 millimoles) of 2,2,6,6-tetramethylpiperidine 1-oxide in 75 ml of N,N-dimethylformamide, after the addition of 1.42 g (14.3 millimoles) of copper(I) chloride, the temperature being kept at from 20° to 35° C. with the aid of an ice bath. After 1 hour, the mixture was poured onto 150 ml of aqueous sodium chloride solution and extracted with methyl tert-butyl ether. The organic phase was first washed with a solution of sodium iodide in 5% strength hydrochloric acid, shaken with aqueous sodium thiosulfate solution, washed with water and then dried over sodium sulfate, after which the solvent was removed under reduced pressure. 27.3 g (92% yield) of ethyl 2,6-dimethyl-8-oxoocta-2,4,6-trien-1-oate were obtained.

EXAMPLE 4

Oxidation of 8-hydroxy-2,5-dimethylocta-2,4,6-trien-1-al

From 50 to 60 ml of oxygen per minute were passed through a stirred solution of 13.95 g (83.9 millimoles) of (all-E)-8-hydroxy-2,6-dimethylocta-2,4,6-trien-1-al and 655 mg (4.2 millimoles) of 2,2,6,6-tetramethylpiperidine 1-oxide in 50 ml of N,N-dimethylformamide, after the addition of 415 mg (4.2 millimoles) of copper(I) chloride, at from 25° to 35° C.

After 3 hours, the reaction mixture was poured onto twice the amount of aqueous sodium chloride solution and extracted with methyl tert-butyl ether, and the extract was washed with water and dried. The solvent was removed under reduced pressure to give 11.25 g (81.6% crude yield) of (all-E)-2,6-dimethylocta-2,4,6-trien-1,8-dial, which were subjected to rapid chromatography over silica gel using 2:1 cylcohexane/ethyl acetate. 9.80 g (71.0% yield) of the desired compound were obtained. $^1$H-NMR (200 MHz, CDCl$_3$): δ=10.20 (d, 1H, J=7.7 Hz), 9.57 (s, 1H), 7.20 (dd, 1H, J=15.4 Hz, 10.8 Hz), 6.98 (dd, 1H, J=10.8 Hz, 1.4 Hz), 6.78 (d, 1H, J=15.4 Hz), 6.12 (d, 1H, J=7.7 Hz), 2.40 (s, 3H), 1.98 (s, 3H)

EXAMPLE 5

Oxidation of 3-methyl-7-(5,5-dimethyl-1,3-dioxan-2-yl)-octa-2,4,6-trien-1-ol

From 50 to 60 ml of oxygen per minute were passed through a stirred solution of 10.0 g (39.6 millimoles) of (all-E)-3-methyl-7-(5,5-dimethyl-1,3-dioxan-2-yl)octa-2,4,6-trien-1-ol and 310 mg (1.98 millimoles) of 2,2,6,6-tetramethylpiperidine 1-oxide in 50 ml of N,N-dimethylformamide, after the addition of 196 mg (1.98 millimoles) of copper(I) chloride, at from 25° to 35° C.

After 7 hours, the reaction mixture was poured onto twice the amount of aqueous sodium chloride solution and extracted with methyl tert-butyl ether. The organic phase was dried and the solvent was removed under reduced pressure, 8.8 g (88.7% crude yield) of (all-E)-3-methyl-7-(5,5-dimethyl-1,3-dioxan-2-yl)octa-2,4,6-trien-1-al being obtained. Crystallization from n-hexane gave 6.9 g (69.6% yield) of the desired aldehyde.

$^1$H-NMR (200 MHz, CDCl$_3$): δ=10.15 (d, 1H, J=7.8 Hz), 7.00 (dd, 1H, J=15.7 Hz, 11.0 Hz), 6.40 (d, 1H, J=15.7 Hz), 6.35 (d, 1H, J=11.0 Hz), 5.98 (d, 1H, J=7.8 Hz), 4.80 (s, 1H), 3.70 (d, 1H), 3.52 (d, 1H), 2.32 (s, 3H), 1.93 (s, 3H), 1.23 (s, 3H), 0.77 (s, 3H).

We claim:

1. A process for the preparation of a polyene aldehyde of the formula I

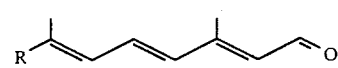

where R is

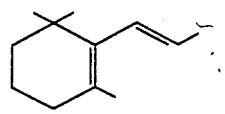

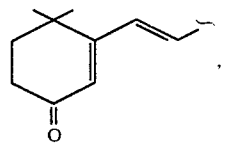

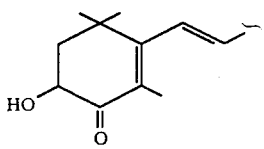

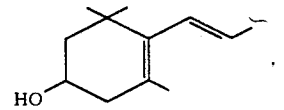

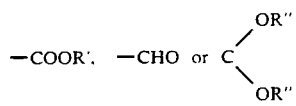

where R' is alkyl, aryl, aralkyl or cycloalkyl and, if desired, may be further substituted, and the radicals R" are each C$_1$-C$_4$-alkyl or together form —CH$_2$—CH$_2$ or —CH$_2$—CH$_2$—CH$_2$— bridges which, if desired, may be further substituted by C$_1$-C$_4$-alkyl, by catalytic oxidation of the corresponding polyene alcohol with oxygen or an oxygen-containing gas, wherein the oxidation is carried out in the presence of the catalyst system comprising 2,2,6,6-tetramethylpiperidine 1-oxide or 4-oxo-2,2,6,6-tetramethylpiperidine 1-oxide and copper(I) chloride.

2. The process of claim 1, wherein (all-E)-retinal is prepared from (all-E)-retinol.

3. A process as claimed in claim 1, wherein the reaction is carried out in the homogeneous phase in a solvent.

4. The process of claim 3, wherein the solvent used is N,N-dimethylformamide, N,N-dimethylacetamide, 1-methyl-2-pyrrolidone, N,N-dimethylpropyleneurea or N,N-dimethylethyleneurea.

5. The process of claim 1, wherein the catalyst components 2,2,6,6-tetramethylpiperidine 1-oxide or 4-oxo-2,2,6,6-tetramethylpiperidine 1-oxide and copper(I) chloride are used in a molar ratio of from 1:0.5 to 1:3.

6. The process of claim 1, wherein the individual catalyst components are each present in an amount of from 1 to 10 mol %, based on the polyene alcohol used.

7. The process of claim 1, wherein the individual catalyst components are each present in an amount of from 5 to 10 mol % based on the polyene alcohol used.

* * * * *